US009636678B2

(12) United States Patent
Briggs

(10) Patent No.: US 9,636,678 B2
(45) Date of Patent: May 2, 2017

(54) SAMPLE VESSEL ASSEMBLY

(71) Applicant: SnapLab Technologies, LLC, Oklahoma City, OK (US)

(72) Inventor: Justin Briggs, Oklahoma City, OK (US)

(73) Assignee: SnapLab Technologies, LLC, Oklahoma City, OK (US)

( * ) Notice: Subject to any disclaimer, the term of this patent is extended or adjusted under 35 U.S.C. 154(b) by 0 days.

(21) Appl. No.: 14/643,565

(22) Filed: Mar. 10, 2015

(65) Prior Publication Data

US 2015/0251175 A1 Sep. 10, 2015

Related U.S. Application Data

(60) Provisional application No. 61/950,510, filed on Mar. 10, 2014.

(51) Int. Cl.
*B01L 3/00* (2006.01)
*G01N 35/00* (2006.01)
*G01N 35/04* (2006.01)

(52) U.S. Cl.
CPC ........ *B01L 3/508* (2013.01); *G01N 35/00732* (2013.01); *B01L 2200/025* (2013.01); *B01L 2200/026* (2013.01); *B01L 2300/041* (2013.01); *B01L 2300/046* (2013.01); *B01L 2300/0858* (2013.01); *G01N 2035/00277* (2013.01); *G01N 2035/00801* (2013.01); *G01N 2035/00831* (2013.01); *G01N 2035/00851* (2013.01); *G01N 2035/00881* (2013.01); *G01N 2035/0405* (2013.01); *Y10T 436/11* (2015.01)

(58) Field of Classification Search
CPC  B01L 3/508; B01L 3/52; B65D 5/001; B65D 5/005; B65D 5/002
USPC ......... 422/551, 554; 206/501; 220/781, 380, 220/4.26
See application file for complete search history.

(56) References Cited

U.S. PATENT DOCUMENTS

| | | | |
|---|---|---|---|
| 337,721 A * | 3/1886 | Wheelwright | ......... B65D 90/08 220/4.12 |
| 3,691,723 A | 9/1972 | Kummer | |
| 3,964,867 A | 6/1976 | Berry | |
| 4,277,259 A | 7/1981 | Rounbehler | |

(Continued)

FOREIGN PATENT DOCUMENTS

WO    2013/192396    12/2013

*Primary Examiner* — Paul Hyun
(74) *Attorney, Agent, or Firm* — Dunlap Codding, P.C.

(57) ABSTRACT

A sample vessel assembly, comprising a base member including a base flange having first and second opposing surfaces, first and second sides intersecting with one another; and a first sidewall extending from the first surface at a distance from the first and second sides; and a lid member, including: a lid flange having third and fourth opposing surfaces, third and fourth sides intersecting with one another; and a second sidewall extending from the third surface at a distance from the third and fourth sides, the second sidewall engageable with the first sidewall such that the first surface of the base flange and the third surface of the lid flange are in an opposing spaced-apart relationship with one another and such that the first and second sidewalls cooperate with one another to define a sample chamber. Further disclosed is a method for automated analysis of samples in a sample vessel assembly.

11 Claims, 8 Drawing Sheets

(56) References Cited

U.S. PATENT DOCUMENTS

| | | | |
|---|---|---|---|
| 4,298,572 | A | 11/1981 | Moffet et al. |
| 4,865,813 | A | 9/1989 | Leon |
| 4,970,053 | A | 11/1990 | Fechtner |
| 5,167,922 | A | 12/1992 | Long |
| 5,181,419 | A | 1/1993 | Thompson |
| 5,381,916 | A * | 1/1995 | Strawder ............ B65D 21/0202 220/212 |
| 5,762,878 | A | 6/1998 | Clark et al. |
| 5,985,218 | A | 11/1999 | Goodale |
| 6,003,706 | A * | 12/1999 | Rosen ................ B65D 81/3816 220/4.26 |
| 6,063,340 | A | 5/2000 | Lewis et al. |
| 6,386,026 | B1 | 5/2002 | Zamfes |
| 6,723,290 | B1 | 4/2004 | Wardlaw |
| 8,101,431 | B2 | 1/2012 | McDevitt et al. |
| 8,146,448 | B2 | 4/2012 | Briscoe et al. |
| 8,182,769 | B2 | 5/2012 | Chavarria |
| 8,342,004 | B2 | 1/2013 | Richards |
| 2004/0200297 | A1 | 10/2004 | Rogers et al. |
| 2007/0295112 | A1 | 12/2007 | Swank et al. |
| 2011/0250106 | A1 * | 10/2011 | Lafond ............. A61B 10/0096 422/551 |
| 2013/0071944 | A1 | 3/2013 | Ulrich et al. |
| 2013/0203172 | A1 | 8/2013 | Wex et al. |
| 2014/0033809 | A1 | 2/2014 | Bransky et al. |

* cited by examiner

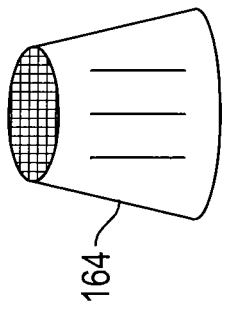
FIG. 8C
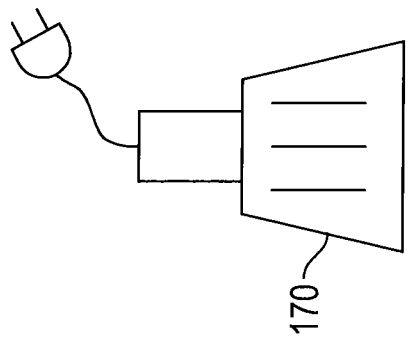
FIG. 8F
FIG. 8B
FIG. 8E
FIG. 8A
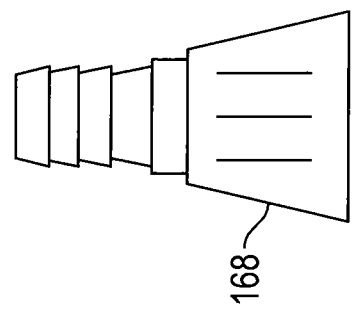
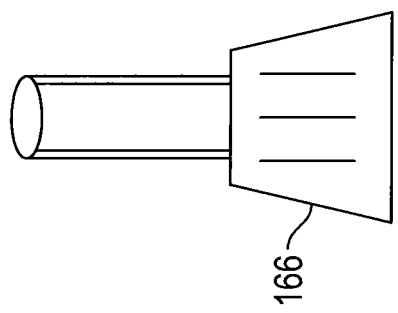
FIG. 8D

SAMPLE VESSEL ASSEMBLY

CROSS-REFERENCE TO RELATED APPLICATIONS

This application claims priority to U.S. Provisional Application Ser. No. 61/950,510, filed on Mar. 10, 2014, the entire content of which is hereby expressly incorporated herein by reference.

BACKGROUND

Many fields and industries require the capture, storage, and analysis of various samples. For example, life sciences and related diagnostic and laboratory testing fields capture, store, and analyze various fluids, such as blood. The environment in which the samples are collected and analyzed is carefully controlled to avoid contamination of the sample, and the volume of the sample required to carry out the desired analysis is generally low. As such, open ended, low volume sample vessels, such as test tubes, have long been used to capture, store, and analyze samples of this type.

Other industries, such as the petrochemical industry, also require the capture, storage, and analysis of various samples. For example, during the process of drilling oil and gas wells, it is desirable to collect and analyze drilling fluids and drill cuttings. Unlike a laboratory setting, the environment at a well site, where drilling fluid and drill cutting samples must be collected, is harsh. Furthermore, the volume of the samples required to carry out the desired analysis can be relatively large.

Some existing sampling and analytical technology allows for using automation and increasing throughput of low volume samples. In some cases, where relatively larger volume samples are used, well plates and test tubes have been implemented to collect and/or analyze such large-volume samples. However, test tubes, well plates, or cuvettes are generally fragile, have a single access point usually through the top, and are not easy to transport, process, and store in non-delicate sampling environments. Further, existing test tubes allow limited sample size and are sub-optimal for mixed-phase samples such as soil, silt, mud, drilling fluids, or other mixed-phase samples. Finally, while existing test tubes or plates allow for simple testing of samples, it can be difficult to reliably and consistently image samples positioned inside existing test tubes or plates.

Accordingly, a need exists for a sample vessel assembly which has a relatively large volume and which is configured to be used with mixed-phase samples. It is to such a sample vessel assembly and to methods of using same in automated analysis systems that the inventive concepts disclosed herein are directed.

BRIEF DESCRIPTION OF THE DRAWINGS

Implementations of the inventive concepts disclosed herein may be better understood when consideration is given to the following detailed description thereof. Such description makes reference to the annexed pictorial illustrations, schematics, graphs, figures, or drawings. The drawings are not necessarily to scale, and certain features and certain views of the drawings may be shown exaggerated, to scale, or in schematic in the interest of clarity and conciseness. Like reference numerals in the figures may represent and refer to the same or similar element or function. In the drawings:

FIGS. 8A-8F show exemplary embodiments of couplings for a port of a sample vessel assembly according to the inventive concepts disclosed herein.

DETAILED DESCRIPTION OF EXEMPLARY EMBODIMENTS

Figure 1:
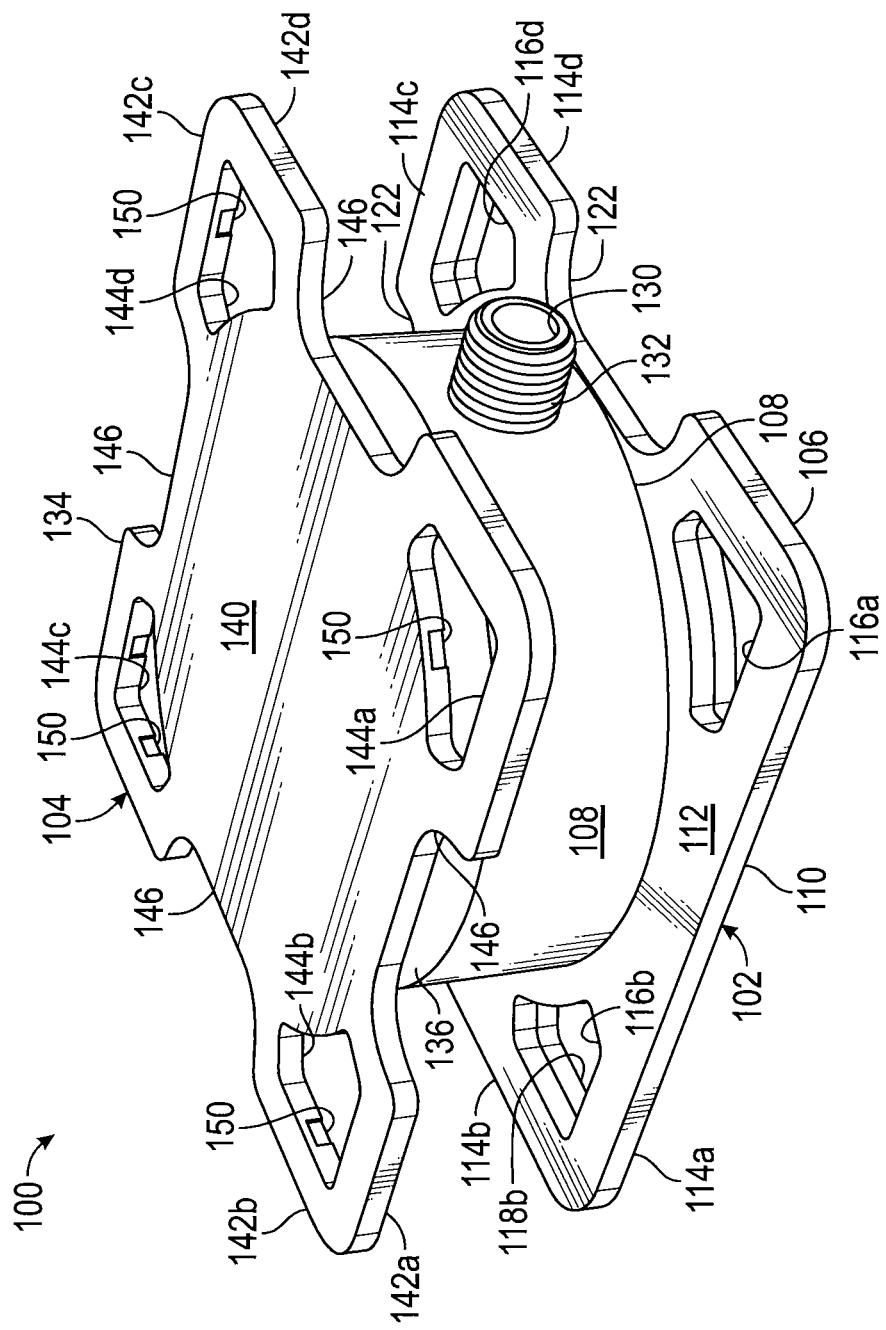
FIG. 1 is a perspective view of an embodiment of a sample vessel assembly according to the inventive concepts disclosed herein.
Figure 2:
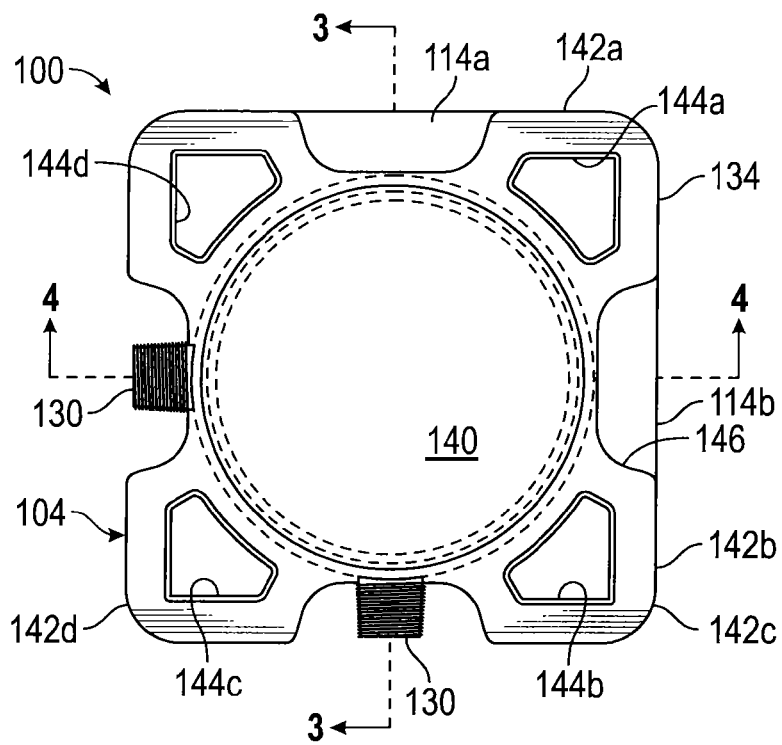
FIG. 2 is a top plan view of the sample vessel assembly of FIG. 1.

Before describing embodiments of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

As used herein the notation "a-n" appended to a reference numeral is intended as merely convenient shorthand to reference one, or more than one, and up to infinity, of the element or feature identified by the respective reference numeral (e.g., 134a-n). Similarly, a letter following a reference numeral is intended to reference an embodiment of the feature or element that may be similar, but not necessarily identical, to a previously described element or feature bearing the same reference numeral (e.g., 148, 148a, 148b, etc.).

Such shorthand notations are used for purposes of clarity and convenience only, and should not be construed to limit the instant inventive concepts in any way, unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As used herein "mixed-phase media," and "mixed-phase sample" are intended to include a sample or media including two or more of the following phases of one or more materials: a solid phase, a fluid phase, a liquid phase, a vapor phase, and a gas phase.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment, and the inventive concept, and the inventive concepts disclosed herein are intended to encompass any and all combinations, subcombinations, and permutations including one or more of the features described or inherently present herein and/or obvious variations thereof.

The inventive concepts disclosed herein are generally directed to sample vessel assemblies and to methods of using same. In some embodiments, sample vessel assemblies according to the inventive concepts disclosed herein may be implemented as large-volume sample vessel assemblies for mixed-phase samples where non-delicate obtaining, handling, or storage of such samples is to be carried out. Further, in exemplary embodiments, sample vessel assemblies according to the inventive concepts disclosed herein may be configured for use as sample cartridges for automated analysis systems. Sample vessel assemblies according to the inventive concepts disclosed herein facilitate sample characterization and analysis by enabling "in-vessel" analysis, reducing contamination, protecting field and laboratory personnel from volatiles or pathogens in samples, allowing "breaking down" of samples to sub-samples or aliquots for various types of distinct testing, enabling automation and high throughput screening, and allowing integration with existing automated analysis systems and methods.

Sample vessel assemblies according to some embodiments of the inventive concepts disclosed herein are modular, and may be configurable for specific analyses and processes. For instance, sample vessel assemblies according to the inventive concepts disclosed herein may be used manually on a bench-top, or may be geared toward automation via automated analysis systems. Further, embodiments of sample vessel assemblies according to the inventive concepts disclosed herein may include optional shaped sides, openings, protrusions, stubs, or other structures for handling, grabbing, stacking, or interlocking or stacking of sample vessel assemblies. Additionally, some embodiments include superstructures configured to allow for easy opening, grabbing and automation from any orientation of the sample vessel assembly, and such superstructures may be triangular, oval, rectangular, square, trapezoid, polygonal, star-shaped, or combinations thereof.

Embodiments of the inventive concepts disclosed herein may be implemented with various ports, couplings, or valves positioned at various locations for sample collection, characterization, and analysis. Further, some embodiments of sample vessel assemblies may be substantially opaque to protect samples from UV or other light damage, or may include one or more transparent portions to allow visual inspection of samples in the sample vessel assembly such as by a spectrophotometer, a spectrometer (e.g., IR), a microscope, or any other desired optical instrument. In addition, embodiments of sample vessel assemblies may be configured for varying containment levels, such as being substantially impermeable to fluids, gasses, air, pressure-rated for any desired pressure, temperature-rated for any desired temperature, or combinations thereof, for example, depending on sample-type and/or desired test or analysis methods.

Figure 3:
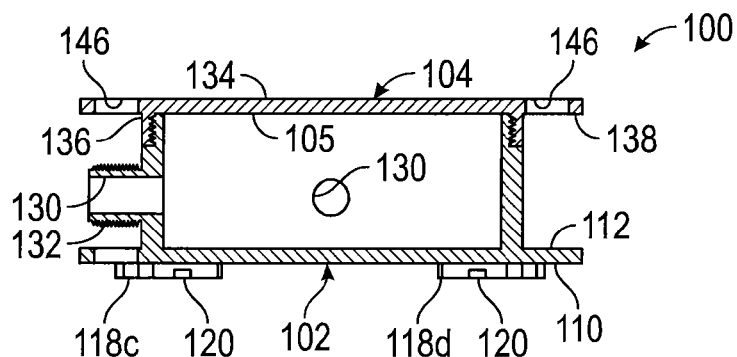
FIG. 3 is a cross-sectional view along line 3-3 of FIG. 2.
Figure 4:
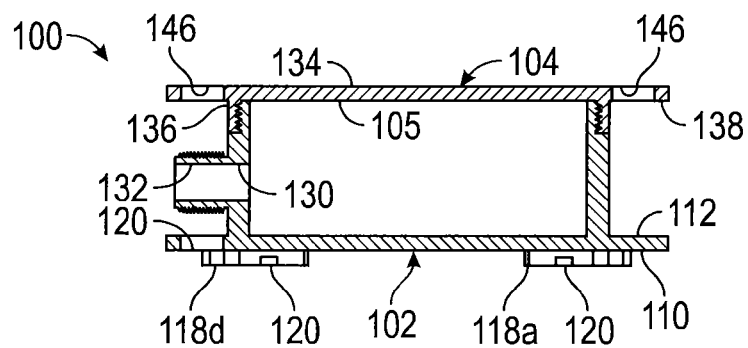
FIG. 4 is a cross-sectional view along line 4-4 of FIG. 2.
Figure 5:
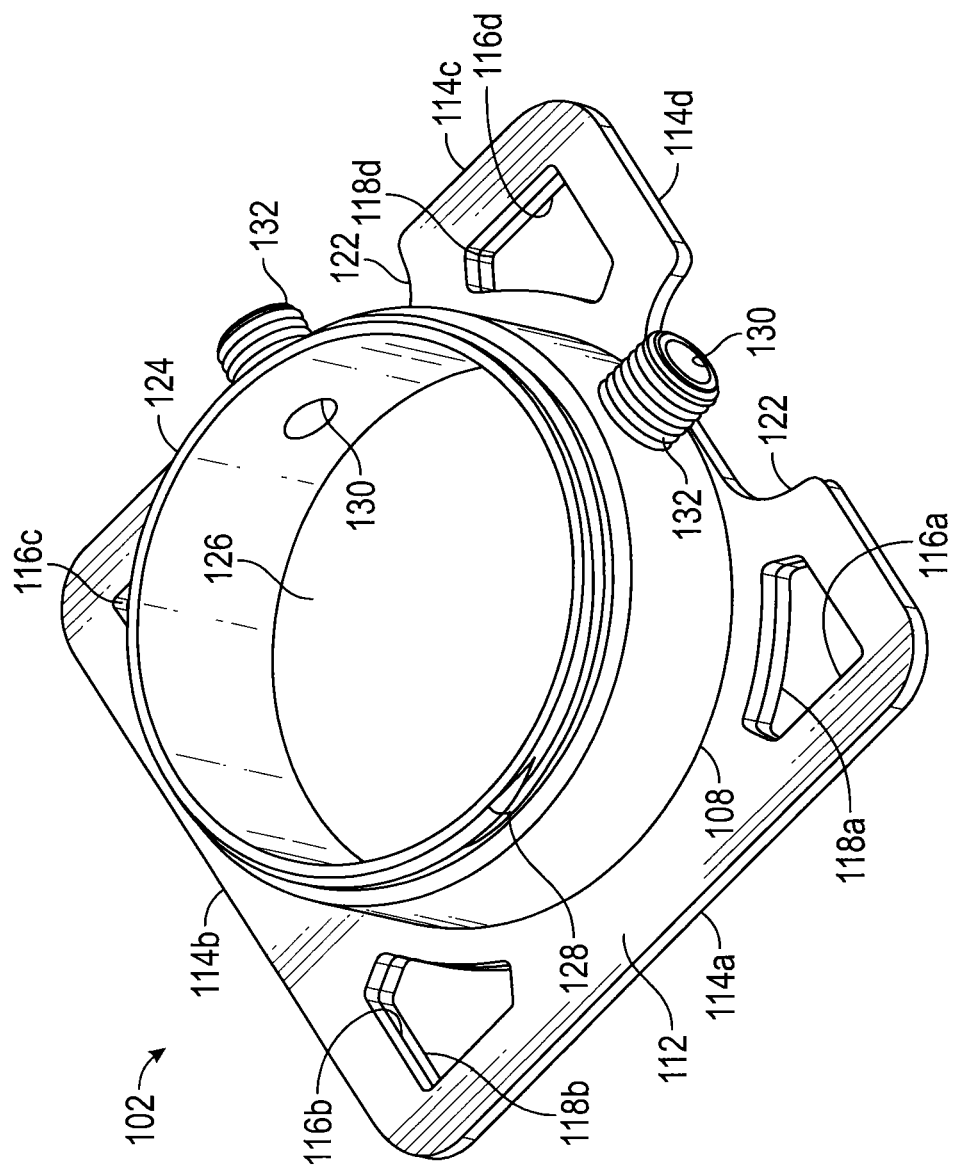
FIG. 5 is a perspective view of an embodiment of a base member according to the inventive concepts disclosed herein.
Figure 6:
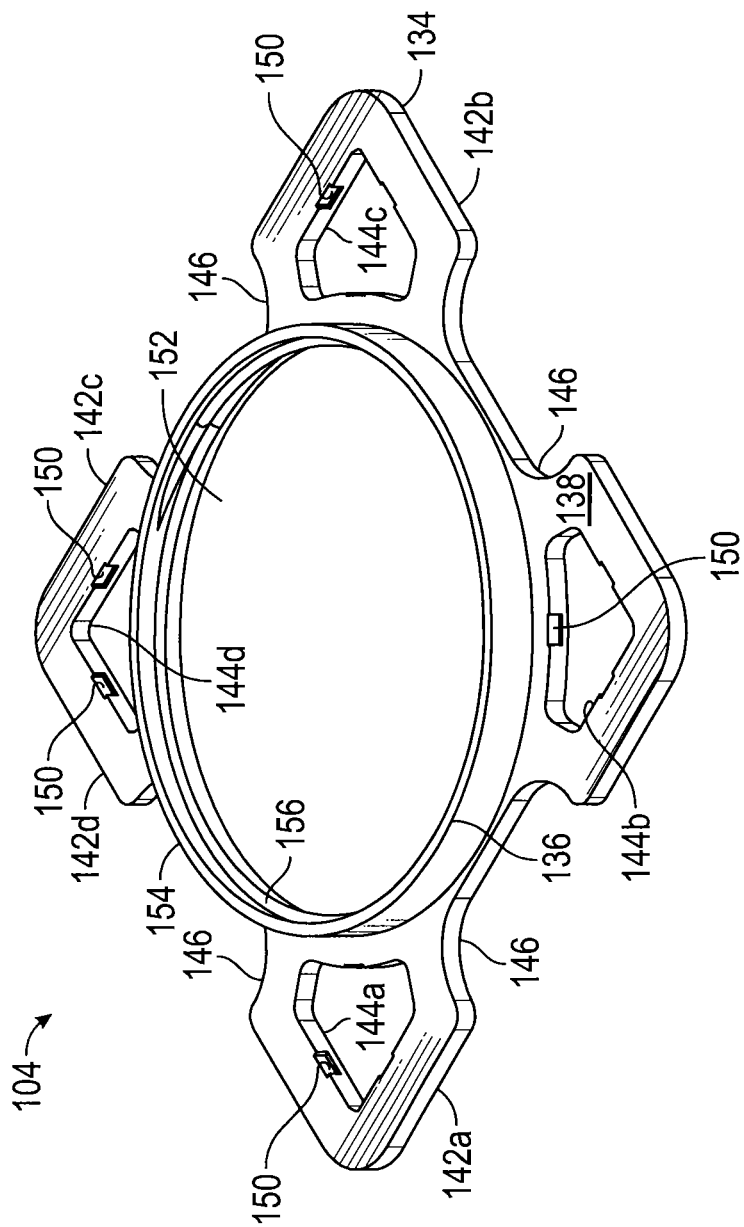
FIG. 6 is a perspective view of an embodiment of a lid member according to the inventive concepts disclosed herein.

Referring now to FIGS. 1-6, shown therein is a sample vessel assembly 100 according to an embodiment of the inventive concepts disclosed herein. The sample vessel assembly 100 includes a base member 102 and a lid member 104 configured to be coupled or otherwise engaged with one another so as to define a substantially fluidly-impermeable sample chamber 105 (FIGS. 3-4).

The base member 102 includes a base flange 106 and a sidewall 108. The base member 102 may be constructed of any desired material such as metals, alloys, non-metals, polymers, glass, ceramic materials, composite materials, plastics, resins, carbon fiber, or combinations thereof, and may be manufactured by any desired method or process such as molding, machining, die cutting, casting, 3D-printing, or combinations thereof. In some embodiments, the base member 102 may be substantially opaque or may include a transparent surface or portion so as to allow visual inspection and/or optical instrument measurements of a sample placed in the sample vessel assembly 100 as will be appreciated by persons of ordinary skill in the art having the benefit of the instant disclosure.

The base flange 106 has opposing surfaces 110 and 112 and sides 114a-d. The surfaces 110 and 112 include openings 116a-d, and attachment protrusions 118a-d. The surfaces 110 and 112 are shown as being substantially flat, although in some embodiments one or both of the surfaces 110 and 112 may include one or more curved (e.g., concave or convex) portions, raised, roughened or textured portions, one or more label portions, one or more bar code or QR code portions, one or more color coded portions, one or more handle or gripping portions, and combinations thereof. Further, in some embodiments, one or both surfaces 110 and 112 may include optional color-coding or other visual or haptic markings indicative of directional orientation of the base member 102, volume of the sample vessel assembly 100, pressure rating of the sample vessel assembly 100, date of manufacture, or any other desired information, as will be appreciated by persons of ordinary skill in the art having the benefit of the instant disclosure.

The openings 116a-d may be formed in the base flange 106 in any desired manner, and may extend completely or partially from the surface 110 to the surface 112. The openings 116a-d may be configured to function as handles or grasping portions so as to allow a user or a robotic arm to securely grasp and/or manipulate the base flange 106. It is to be understood that the openings 116a-d may have any desired shape and size. Further, in some embodiments the openings 116a-d may be omitted, and in some embodiments any desired number of openings 116a-d may be implemented, such as one, two, three, or more than four openings 116a-n. The openings 116a-d are shown as being offset from the sides 114a-d, but it is to be understood that in some embodiments the openings 116a-d may intersect with the sides 114a-d.

The attachment protrusions 118a-d are shown as extending from the surface 110 adjacent to the openings 116a-n. The attachment protrusions 118a-n include lateral portions 120 sized and configured to be matingly received in corresponding attachment notches formed in the lid flange 104 as described below. It is to be appreciated that any desired number of attachment protrusions 118a-n may be implemented with the inventive concepts disclosed herein. Further, in some embodiments the attachment protrusions 118a-d may be omitted.

The sides 114a and 114b are shown as being substantially straight, and the sides 114c and 114d are shown as including notches 122 formed therein. It is to be understood that in some embodiments the notches 122 may be omitted, and in some embodiments the sides 114a and 114b may include one or more notches 116 formed therein. The notches 122 may be configured to allow easier access to the sample inside the sample chamber from the direction of the base member 102. Further, the sides 114a-d may have any desired shape, curvature, or profile, including being concave, convex, angled, or including one or more portions having different curvature or profile, as will be appreciated by a person of ordinary skill in the art having the benefit of the instant disclosure.

It is to be appreciated that while the four sides 114a-d are shown as intersecting with one another to define a substantially square superstructure of the base flange 106, base flanges 106 according to the inventive concepts disclosed herein may have any desired numbers of sides 114a-n, such as one, two, three, five, six, seven, or more than seven sides 114a-n. Further, base flanges 106 according to the inventive concepts disclosed herein may have any desired shapes or superstructures, such as circular, oval, triangular, rectangular, trapezoid, pentagonal, hexagonal, heptagonal, octagonal, polygonal, star-shaped, irregularly-shaped, or combinations thereof.

The sidewall 108 extends from the surface 112 such that the sidewall 108 is separated at a distance from the sides 114a-d and/or the openings 116a-d, and such that the openings 116a-d are positioned between the sidewall 108 and the sides 114a-d. However, in some embodiments the sidewall 108 may abut or intersect with one or more of the openings 116a-d, and/or may abut or intersect with one or more of the sides 114a-d. The sidewall 108 may be attached to the surface 112 in any desired fluidly-impermeable manner, such as via welding, joints, seams, or adhesives, or combinations thereof. In some embodiments, the sidewall 108 and the base flange 106 may be formed as a unitary body, such as via casting, machining, molding, or 3D printing, for example. While the sidewall 108 is shown as being substantially centered relative to the surface 112, in some embodiments the sidewall 108 may be offset relative to the surface 112, such that the sidewall 108 is separated at a first distance from one of the sides 114a-d, and a second distance different from the first distance from another one of the sides 114a-d.

The sidewall 108 is shown as being substantially circular, however, embodiments of a sidewall 108 according to the inventive concepts disclosed herein may be implemented with any desired shape, curvature, or cross-sections, such as oval, circular, triangular, rectangular, square, polygonal, or combinations thereof. The sidewall 108 includes an end 124 extending at any desired distance from the surface 112, and a bottom 126 which may be substantially flat, or may have any desired curvature (e.g., concave or convex) in some embodiments, depending, for example, on the desired volume of the sample chamber 105. Further, in some embodiments the bottom 126 may be substantially transparent and may include any desired curvature so that the bottom 126 may serve as a lens to allow optical instruments to carry out optical measurements or obtain readings from inside the sample chamber 105.

The end 124 includes threads 128 formed therein for matingly engaging the top member 104 as described below. While the threads 128 are shown as external threads 128, in some embodiments the threads 128 may be implemented as internal threads 128. Additionally, in some embodiments the threads 128 can be omitted. Further, in some embodiments any other suitable structures of devices may be used to engage or couple the lid member 104 and the base member 102 to one another, such as press-fittings, lips, flanges, snap-in features, gaskets, sleeves, clamps, or combinations thereof.

The sidewall 108 further includes one or more ports 130 formed therein. The ports 130 are in fluid communication with the sample chamber 105 and may include threaded portions 132 configured to be coupled with any desired coupling, such as a valve, cap, seal, or sensor fitting, examples of which are described with reference to FIGS. 8A-8F below. It is to be understood that any desired number of ports 130 may be implemented in some embodiments, such as one, three, four, or more than four ports 130. Further, in some embodiments, the ports 130 may be omitted, or one or more ports 130 may be in fluid communication with the sample chamber 105 via any desired location along the sidewall 108, the base member 102 and/or the lid member 104. In some embodiments one or more ports 130 may protrude or may be level with the sidewall 108. For example, a top port 130 (e.g., fluidly coupled with a headspace above a level of a sample inside the sample chamber 105) may be used to extract a supernatant or gas-chromatograph aliquot, a mid-height port 130 (e.g., fluidly coupled with the sample chamber 105 so as to be submerged or at least partially below a level of a sample in the sample chamber 105) may be used for extracting a volume of sample, and a bottom port 130 (e.g., fluidly coupled with the sample chamber 105 at or below the level of the bottom 126) may be used as a drain.

The lid member 104 may be implemented similarly to the base member 102 and includes a lid flange 134 and a sidewall 136. The lid flange 134 has surfaces 138 and 140 and sides 142a-d intersecting with one another. The lid flange 134 further includes openings 144a-d formed therein. In some embodiments, the lid member 104 may include a transparent portion such that the sample chamber 105 is observable (e.g., via an optical instrument), while in some embodiments, the lid member 104 may be opaque.

The sides 142a-d may include notches 146 formed therein. The notches 146 may be implemented similarly to the notches 122 and are configured to allow easy access to the ports 130 from the direction of the lid member 102 as will be appreciated by persons of ordinary skill in the art having the benefit of the instant disclosure. In some embodiments, the notches 146 may abut or intersect with one or more of the openings 144a-d and/or may abut or intersect the sidewall 136. Any desired number of sides 142a-d may be implemented with the inventive concepts disclosed herein, such as one side 142, two sides 142, three sides 142, or more than four sides 142.

The openings 144*a-d* may be configured to matingly (e.g., slidably or removably) receive the attachment protrusions 118*a-d* of the base flange 106 therein, and may include notches 150 formed therein and configured to matingly receive (e.g., removably or slidably) the lateral portion 120 of the attachment portions 118*a-d* therein, as will be appreciated by persons of ordinary skill in the art having the benefit of the instant disclosure. It is to be understood that any desired openings 144*a-d* may be implemented such as a single opening 144, two openings 144, three openings 144, or more than four openings 144 in some embodiments. Further, in some embodiments, the openings 144*a-d* may be omitted. In some embodiments, the openings may be separated at a distance from the sides 142*a-d* and the sidewall 136, while in some embodiments one or more of the openings 144*a-d* may abut or intersect one or more of the sides 142*a-d* and/or the sidewall 136.

The sidewall 136 may be implemented similarly to the sidewall 108 and extends from the surface 138 at a distance from the sides 142*a-n* and/or from the openings 144*a-d* such that the openings 144*a-d* are positioned between the sidewall 136 and the sides 144*a-d*. The sidewall 136 includes a bottom 152 and end 154 including threads 156 configured to matingly engage the threads 128 of the sidewall 108 such that the sidewalls 108 and 136 cooperate to define the sample chamber 105 and such that the surface 112 of the base flange 106 and the surface 138 of the lid flange 134 are in an opposing spaced-apart relationship with one another. The sidewall 136 is engageable with the sidewall 108 in a substantially fluid-impermeable manner, such that the sample chamber 105 is substantially fluidly sealed or fluid-impermeable. Further, in some embodiments, the sidewall 136 is engageable with the sidewall 108 such that the sample chamber 105 is gas-impermeable and/or can maintain or withstand a predetermined amount of pressure or vacuum.

In some embodiments, gaskets, seals, sleeves, sealant tape or sealant materials, or any other desired devices or material may be implemented with the ends 124 and 154 and/or with the threads 128 and/or 156 so as to provide a substantially gas-impermeable and/or a substantially fluid-impermeable engagement of the sidewalls 108 and 136 with one another. Further, in some embodiments, the sidewall 136 and the sidewall 108 may be formed as a unitary component, or may be engageable with one another in any desired substantially fluid- and/or gas-impermeable manner, such as via welds, seams, joints, adhesives, ultrasonic welds, clamps, or combinations thereof.

Figure 7:
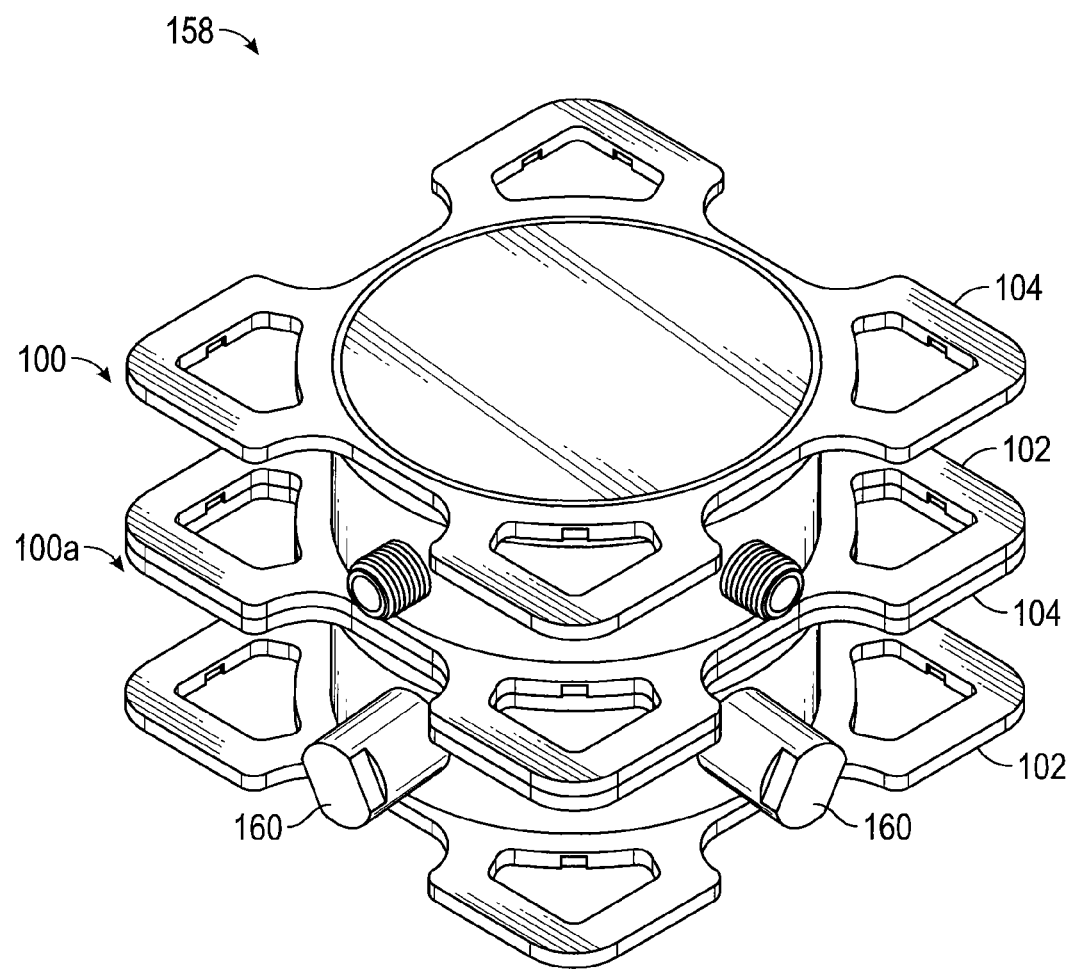
FIG. 7 is a perspective view of a stack of sample vessel assemblies according to the inventive concepts disclosed herein.

Referring now to FIG. 7, shown therein is a stack 158 including sample vessel assemblies 100 and 100*a* stacked onto one another such that the protrusions 118*a-d* of the sample vessel assembly 100 are matingly received in the openings 144*a-d* of the sample vessel assembly 100*a* and/or such that the lateral portions 120 of the sample vessel assembly 100 are matingly received in the notches 150 of the sample vessel assembly 100*a*, so that the surface 110 of the base flange 106 is positioned adjacent to or in contact with the surface 138 of the lid flange 134. In some exemplary embodiments, the openings 116*a-d* may be substantially aligned with the openings 144*a-d*, or the openings 116*a-d* and the openings 144*a-d* may be offset relative to one another. Any desired number of sample vessel assemblies 100 may be stacked in similar manner, such as three, four, five, or more than five sample vessel assemblies 100. Seal caps 160 are shown as being coupled with the threaded portions 132 of the ports 130 of the sample vessel assembly 100*a* so as to close the ports 130 in a substantially fluid-impermeable manner. The stack 158 may be used to transport the sample vessel assemblies 100 and/or to store sample vessel assemblies 100 short-term or long-term.

Referring now to FIGS. 8A-8F, shown therein are examples of couplings such as valves, seals, caps, connectors, couplings, or sensor fittings that may be implemented with one or more ports 130 of sample vessel assemblies 100 according to embodiments of the inventive concepts disclosed herein.

As shown in FIG. 8A, in some embodiments a seal cap 160 may be implemented with a port 130 of a sample vessel assembly 100. The seal cap 160 may be implemented in some embodiments by being threadingly engaged with the threaded portion 132 of one or more ports 130 to lock, seal, or close the port 130. The seal cap 160 may be coupled with the port 130 via a pressure seal or lock in a substantially gas-impermeable and/or substantially fluid-impermeable manner. Further, the seal cap 160 may be configured to withstand a predetermined high-pressure or vacuum and may be transparent or opaque in some embodiments.

As shown in FIG. 8B, in some embodiments a membrane 162 may be implemented with one or more ports 130 of a sample vessel assembly 100 according to the inventive concepts disclosed herein. The membrane 162 may be coupled with the threaded portion 132 of one or more of the ports 130, and includes a septum of rubber or other elastomeric material to allow for easy sub-sampling of gas, liquids, or solids (e.g., aliquot via a probe or syringe) from the sample chamber 105. In some embodiments, the membrane 162 may be compression-fitted or otherwise engaged with the port 130, and can include a sealed cap (e.g., similar to the seal cap 160). The membrane 162 may be substantially gas-impermeable and/or substantially fluid-impermeable, and may be configured to withstand atmospheric or low pressure. Further, the membrane 162 may be positioned at any desired height along the sidewall 108, or may be positioned on the lid member 104 in some embodiments.

As shown in FIG. 8C, in some embodiments a sieve 164 may be implemented with a port 130 of a sample vessel assembly 100 according to the inventive concepts disclosed herein. The sieve 164 may be coupled with the threaded portion 132 of one or more ports 130, or may be positioned under a seal cap 160 coupled with one or more ports 130 in some embodiments. The sieve 164 may be used to remove liquids and/or wash solids from the sample chamber 105, and may be configured so as to keep predetermined size particulates inside the sample chamber 105. The sieve 164 may be formed in the sidewall 108, in the lid member 104, or may be attachable to the end 124 of the sidewall 108 so as to extend across the width of the sample chamber 105 in some embodiments.

As shown in FIG. 8D, in some embodiments a hose coupling 166 may be implemented with a port 130 of a sample vessel assembly 100 according to the inventive concepts disclosed herein. The hose coupling 166 may be threadingly or otherwise engaged with the threaded portion 132 and/or otherwise engaged with the port 130 and may be pressure-sealed or locked. The hose coupling 166 may be used to withdraw water, air, sample, or to drain the sample chamber 105 and may be configured to withstand any desired pressure including relatively high-pressures.

As shown in FIG. 8E in some embodiments a valve coupling 168 may be implemented with a port 130 of a sample vessel assembly 100 according to the inventive concepts disclosed herein. The valve coupling 168 which may be implemented as a twist-on compression fitting or locking and may be a one-way valve coupling 168 (e.g., allowing flow or material in one direction and preventing flow of material in an opposite direction) or two-way valve coupling 168 (e.g., allowing bi-directional flow of material), and may be water or air tight. The valve coupling 168 may be used to withdraw and/or introduce water, air, solution, or to drain the sample chamber 105, and can be configured to withstand high-pressures in some embodiments.

As shown in FIG. 8F, in some embodiments a sensor fitting 170 may be implemented with a port 130 of a sample vessel assembly 100 according to the inventive concepts disclosed herein. The sensor fitting 170 may be coupled with the port 130, and may be configured to interface with any desired sensor, probe, or device, such as temperature, pressure, chemical receptor-based sensors (e.g., configured so sense, detect, or measure C1-C10 hydrocarbon gas species, organic acids, inorganic compounds, including but not limited to: $N_2$, Ar, $O_2$, $H_2O$, He, $H_2$, sulfur-containing compounds such as $SO_2$, COS, $CS_2$, ethene, oxygen—ambient and/or dissolved, gas, or liquid-based probes, CO, $CO_2$, specific C1 species, pH of H+ probes), semi-permeable membrane extraction, mass spectroscopy, and combinations thereof. In some embodiments, the sensor fitting 170 may include one or more probes, detectors, or sensors which may be at least partially positioned inside the sample chamber 105 via the port 130, such as by being submerged in or otherwise contacting a fluid or liquid sample in the sample chamber 105, or by being position above a level or fluid or liquid sample in the sample chamber 105 (e.g., in a headspace above the sample), or combinations thereof.

Embodiments of sample vessel assemblies 100 according to the inventive concepts disclosed herein may be labeled, or otherwise marked or associated with an unique identifier (e.g., a bar code, a QR code, an RFID tag, visual or haptic markings) identifying one or more of: the sample vessel assembly 100, a sample contained in the sample vessel assembly 100, location and/or time the sample was obtained. Further, sample vessel assemblies 100 may be marked or otherwise associated with the identity of obtaining person, destination for the sample, special handling instructions, nature of the sample, requested tests, storage instructions, shipping instructions, or any other desired information pertinent to the sample vessel assembly 100 or to a volume of sample contained therein, or any other feature, attribute, or identifying information relating to a sample positioned in the sample chamber 105 of a sample vessel assembly 100.

It is to be appreciated that sample vessel assemblies 100 according to the inventive concepts disclosed herein may be provided in one or more modular sizes, may include shallower, larger-diameter sample chambers 105, deeper, narrower-diameter sample chambers 105, or offset ports 130 and angled (e.g., about 90° or any desired angle) ports 130 which may be implemented as a single fill-size port 130, for example.

In use, a user may introduce any desired volume, weight, or amount of sample in the sample chamber 105 of a sample vessel assembly 100 in any desired manner. In some embodiments, the user may disassemble the sample vessel assembly 100 by uncoupling or disengaging the base member 102 and the lid member 104 from one another, or may simply obtain a base member 102 where the sample vessel assembly 100 is shipped or provided to the user as a disassembled kit. The user may introduce any desired amount volume or weight of sample into the sample chamber 105 such as by placing the sample inside the sidewall 108. The user may then assemble the sample vessel assembly 100 by engaging or coupling the lid member 104 with the base member 102. In some embodiments, a volume, amount, or weight of a sample may be introduced into the sample chamber 105 via one or more of the ports 130 which may be sealed such as via a seal cap 160, for example. The user may conveniently and easily access the one or more ports 130 from the direction of the base member 102 and/or from the direction of the lid member 104 via the notches 122 and 146, respectively.

Once the base member 102 and the lid member 104 are engaged with one another in a fluidly-impermeable manner, and/or one the one or more ports 130 are closed or sealed, the user may associate any desired unique identifiers with the sample vessel assembly 100, and may store, ship, or transport the sample vessel assembly 100 to any desired location for processing and/or storage. The user may stack any desired number of sample vessel assemblies 100 such as in a stack 158 as described above.

Figure 9:
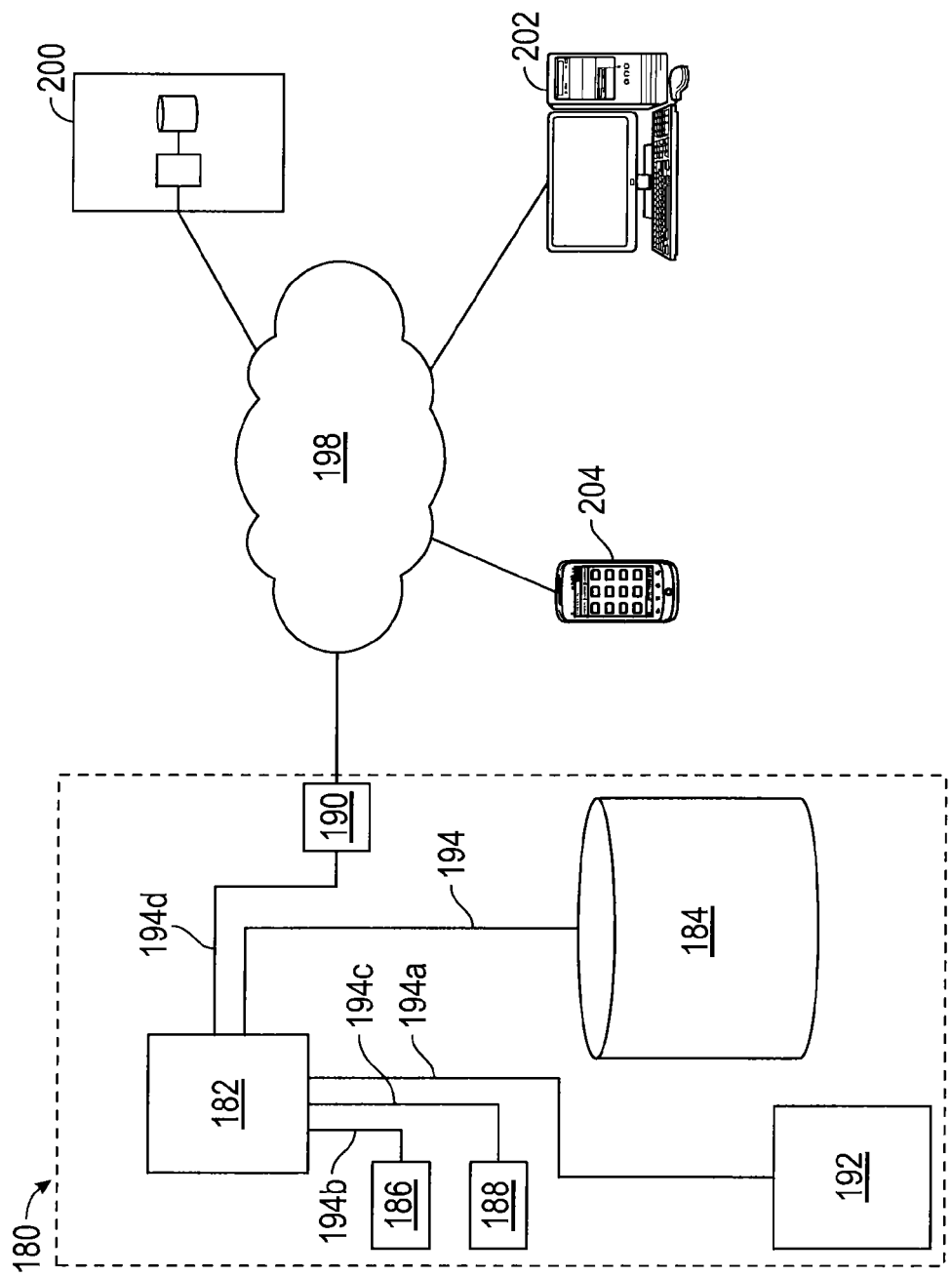
FIG. 9 is a diagram of an exemplary embodiment of an automated analysis system configured to be implemented with sample vessel assemblies according to the inventive concepts disclosed herein.

Referring now to FIG. 9, in some embodiments, sample vessels assemblies 100 according to the inventive concepts disclosed herein may be implemented with an automated analysis system 180. The automated analysis system 180 includes a controller 182, one or more memory 184, an input device 186, and output device 188, an I/O port 190, and a sample analyzer 192. The controller 182 may include at least one processor such as a digital signal processor, a single processor or multiple processors working together to execute the logic described herein. Exemplary embodiments of the controller 182 include a digital signal processor (DSP), a central processing unit (CPU), a field programmable gate array (FPGA), a microprocessor, a multi-core processor, and combinations thereof. The controller 182 is configured to bi-directionally communicate (e.g., exchanging data and or signals) with the memory 184 via a path 194 which may be implemented as a data bus. The controller is also capable of bi-directionally communicating with the sample analyzer 192 via path 194*a*, with the input device 186 via a path 194*b*, with the output device 188 via a path 194*c*, and with the I/O port 190 via a path 194*d*.

The memory 184 stores processor executable code and may be implemented as any desired non-transitory processor-readable medium, such as random access memory (RAM), a CD-ROM, a hard drive, a solid state drive, a flash drive, a memory card, a DVD-ROM, a floppy disk, an optical drive, and combinations thereof, for example. It is to be understood that while the memory 184 is shown located in the same physical location as the automated analysis system 180, in some embodiments the memory 184 may be located remotely from the automated analysis system 180 and may communicate with the controller 182 via a network 198. Additionally, in some embodiments more than one memory 184 may be implemented, with one or more memory 184 being located in the same physical location as the automated analysis system 180, and one or more memory 184 being located in a remote physical location from the automated analysis system 180. The physical location(s) of the memory 184 can be varied, and the memory 184 may be implemented as a "cloud memory," e.g., one or more memory 184 which is partially or completely based on or accessed using the network 198.

The input device 186 transmits data to the controller 182, and can be implemented as a keyboard, a mouse, a touchscreen, a camera, a cellular phone, a tablet, a smart phone, a PDA, a microphone, a network adapter, a QR code reader, a bar code reader, an optical imager, an RFID reader, or combinations thereof, for example. The input device 186 may be located in the same physical location as the automated analysis system 180, or may be remotely located and/or partially or completely network-based.

The output device 188 transmits information from the controller 182 to a user, such that the information can be perceived by the user. For example, the output device 188 can be implemented as a server, a computer monitor, a cell phone, a tablet, a speaker, a website, a PDA, a fax, a printer, a projector, a laptop monitor, and combinations thereof. The output device 188 can be physically co-located with the automated analysis system 180, or can be located remotely from the automated analysis system 180, and may be partially or completely network based (e.g., a website). As used herein the term "user" is not limited to a human, and may comprise a human, a computer, a web server, a database, a host system, a smart phone, a tablet, and combinations thereof, for example.

The I/O port 190 may be implemented as any desired computer port such as an optical port, a wireless transceiver, an Ethernet port, a USB port, an HDMI port, and is configured to transmit one or more signals over the network 198 and/or to receive one or more signals from the network 198.

The sample analyzer 192 may be operably coupled with one or more sample vessel assemblies 100 according to the inventive concepts disclosed herein and to carry out any desired test, measurement, reading, or analysis of one or more properties of a sample positioned in the sample chamber 105 of the sample vessel assembly 100 and to transmit one or more signals indicative of data, measurements, properties, attributes, or features of the analyzed sample to the controller 182. In some embodiments, the sample analyzer 192 may include at least one processor coupled with a non-transitory processor-readable medium storing processor-executable code or instructions.

As will be appreciated by persons of ordinary skill in the art having the benefit of the instant disclosure, the sample analyzer 192 may be implemented as any desired manual or automated device or instrument, such as a microscope, a chromatograph, an MRI imager, a spectrophotometer, a DNA sequencing device, Raman spectroscopy device, ultraviolet or visual spectroscopy device, temperature measuring device, or X-ray fluorescence device. In some embodiments, the sample analyzer 192 may include one or more manual or automated probes, manipulation arms, movable belts, trays, stages, or turntables, fluid pumps, gas pumps, robotic probes or arms configured to move a sample vessel assembly 100, ovens, pressurized or fluid-impermeable chambers, or combinations thereof, for example. Any desired number of sample analyzers 192 may be implemented with the automated analysis system 180, such as a single sample analyzer 192, two or more sample analyzers 192, or a plurality of sample analyzers 192. Further, one or more sample analyzers 192 may be physically co-located with the automated analysis system 180, and in some embodiments, one or more sample analyzers 192 may be remotely located from the automated analysis system 180 and may exchange signals and/or data with the automated analysis system 180 via the network 198.

Figure 10:
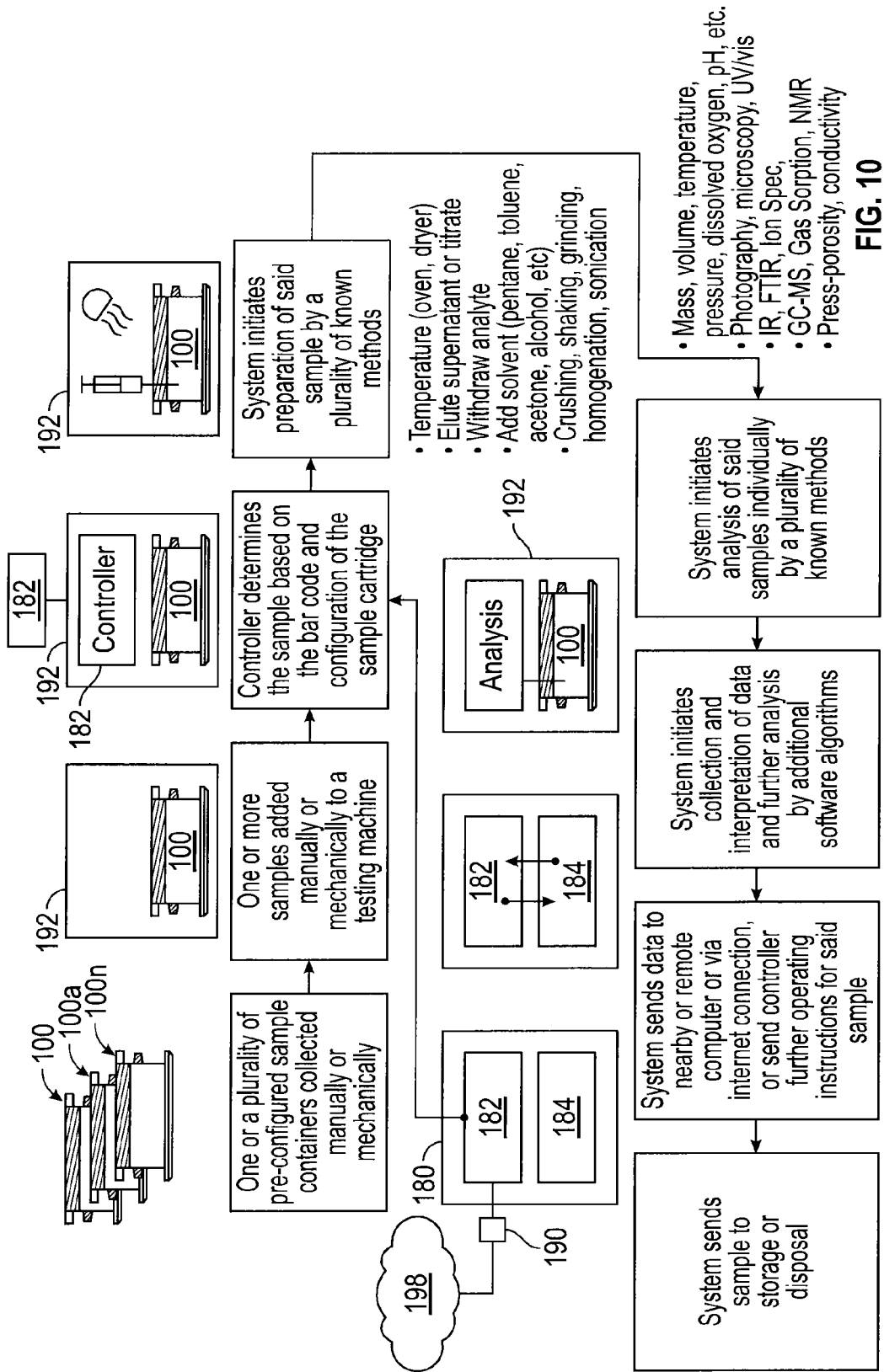
FIG. 10 is a diagram of a process of using a sample vessel assembly according to the inventive concepts disclosed herein with an automated analyzer system.

The network 198 permits bi-directional communication of information and/or data between the automated analysis system 180 and one or more remote devices such as a web server 200, a computer 202, and/or a mobile device 204 (e.g., a smartphone, or a tablet). The network 198 may interface with the I/O port 190 of the automated analysis system 180 in a variety of ways, such as by optical and/or electronic interfaces, and may use a plurality of network topographies and protocols, such as Ethernet, TC/IP, circuit switched paths, or combinations thereof, for example. For example, the network 198 can be implemented as the World Wide Web (or Internet), a local area network (LAN), a wide area network (WAN), a metropolitan network, a wireless network, a cellular network, a GSM-network, a CDMA network, a 3G network, a 4G network, a satellite network, a radio network, an optical network, a cable network, a public switched telephone network, an Ethernet network, and combinations thereof, and may use a variety of network protocols to permit bi-directional interface and communication of data and/or information between the automated analysis system 180 and the one or more remote devices or processors. The automated analysis system 180 may be deployed in the field (e.g., installed locally or as a mobile laboratory vehicle), or may be deployed in a central location where field or other samples are received and processed Referring now to FIG. 10, an embodiment of a method of using a sample vessel assembly 100 with the automated analysis system 180 is shown therein. Generally, one or a plurality of sample vessels assemblies 100 (100*a*-100*n*) are used to collect one or more samples, manually or mechanically as described above. One or more sample vessel assemblies 100 are added manually or mechanically to the sample analyzer 192 of the automated analysis system 180.

The controller 182 may provide one or more control or drive signals to the sample analyzer 192 to cause the sample analyzer 192 to obtain a unique identifier of the sample vessel assembly 100 and/or the sample in the sample chamber 105, such as by scanning or otherwise reading a unique identifier of the sample vessel assembly 100, which may be implemented as a label, a sample vessel number, a bar or QR code, an RFID tag, or the sample may be manually identified by a user providing input to the automated analysis system 180 (e.g., via the input device 186).

The controller 182 and/or the sample analyzer 192 may carry out any desired calibration steps, which may vary based on the type of sample vessel assembly 100, the type of sample, or the type of sample analysis desired, for example.

The controller 182 may initiate sample preparation by the sample analyzer 192 via any desired method. For example, the sample may be heated in an oven or a dryer, a volume of supernatant may be eluted or titrated, analyte may be withdrawn, a solvent or other compound may be added to the sample such as pentane, toluene, acetone, alcohols, or any other desired chemical, or combinations thereof. Further, the sample may be mechanically processed such as by crushing, shaking, grinding, homogenizing, or sonification, or combinations thereof.

The mass, volume, temperature, pressure, dissolved gasses, pH, or any other desired property, component, feature, or attribute of the sample may be measured by the sample analyzer 192 using any desired method such as photography, microscopy, ultraviolet or visible, infra-red, Fourier transform infrared spectroscopy, ion spectrum gas chromatography or mass spectroscopy, gas sorption, nuclear magnetic resonance, pressure-porosity, conductivity, or combinations thereof. The sample analyzer 192 may transmit one or more signals to the controller 182 indicative of any of the properties, attributes, components, or features of the sample measured, read, or determined as described above.

The controller 182 may receive, collect, store, and interpret data indicative of properties of a sample in the sample chamber 105 of the sample vessel assembly 100 in any desired manner, such as by storing raw or processed data in the memory 184 and/or by processing data by executing processor-executable code stored in the memory 184. The controller 182 may also transmit one or more signals (e.g., via the I/O port 190) indicative of sample data, including the unique identifier for the sample and/or the sample vessel assembly 100 to a remote device or processor such as the web server 200 (e.g., hosting a database), computer 202, or mobile device 204, over the network 198, for example.

The processed sample vessel assembly 100 may be removed from the sample analyzer 192 of the automated analysis system 180 and may be stored as appropriate, or may be disposed of in accordance with any applicable disposal protocols or regulations.

The sample analyzer 192 and/or the automated analysis system 180 may be used to carry out any desired test of a sample positioned in the sample chamber 105 of a sample vessel assembly 100. For example, the sample analyzer 192 may carry out visual or optical characterization of the sample, by measuring, detecting, calculating, or otherwise determining the lithology, color, porosity, iridescence, or particle size of the sample. Further, the sample analyzer 192 may carry out microscopy, photography UV and/or visual specophotometry with the sample. In some embodiments, the sample analyzer and/or the controller 182 may execute software or processor-executable code to analyze microscopic and macroscopic photography (e.g., average color values, point distribution, particle size, etc.) of the sample. Further, in some embodiments the sample analyzer 192 may carry out physical characterization of the sample, such as measuring dissolved oxygen and/or viscosity of the sample. In some embodiments, the sample analyzer and/or the controller may conduct analytical characterization of the sample, such as via infra-red spectroscopy, Raman spectroscopy, Gas Chromatography, Gas Chromatography—mass spectroscopy, high-pressure liquid chromatography, nuclear magnetic resonance, Fourier transform infrared spectroscopy, ion spectroscopy etc. Further, in some embodiments the sample analyzer 192 may carry out total organic carbon analysis by acidization, or may carry out Fischer Assay, X-ray diffraction, X-ray crystallography, X-ray fluorescence, Wavelength-dispersive X-ray spectroscopy, energy-dispersive X-ray spectroscopy, gas sorption, pyconometry, porosimetry, or any other desired test or analytical method.

Further, in some embodiments the memory 184 of the automated analysis system 180 may be provided with any desired algorithm to trigger procedural modifications (what analysis or step to carry out next) based on results, signals, or data provided to the controller 182 by the sample analyzer 192. Further, multiple sample vessel assemblies 100 may be preconfigured for varied testing regimens or sequences such as taking any desired number (e.g., 1-12) samples rapid-fire, then sending each sample to a different sample analyzer 192 and/or a different automated analysis system 180 for preparation and analysis.

From the above description, it is clear that the inventive concepts disclosed and claimed herein are well adapted to carry out the objects and to attain the advantages mentioned herein, as well as those inherent in the instant inventive concepts. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or defined in the appended claims.

What is claimed is:

1. A sample vessel assembly, comprising:
   a base member including:
      a base flange having first and second opposing surfaces and first and second sides intersecting with one another; and
      a first sidewall extending from the first surface at a distance from the first and second sides; and
   a lid member, including:
      a lid flange having third and fourth opposing surfaces and third and fourth sides intersecting with one another; and
      a second sidewall extending from the third surface at a distance from the third and fourth sides, the second sidewall engageable with the first sidewall such that the first surface of the base flange and the third surface of the lid flange are in an opposing spaced-apart relationship with one another and such that the first and second sidewalls cooperate with one another to define a sample chamber,
   wherein the base flange further includes at least one opening formed therein and at least one attachment protrusion extending from the second surface adjacent to the at least one opening.

2. The sample vessel assembly of claim 1, wherein the first sidewall and the second sidewall are threadingly engageable with one another.

3. The sample vessel assembly of claim 1, wherein the lid flange further includes at least one opening for matingly receiving the attachment protrusion therein of a base flange of another vessel assembly.

4. A sample vessel assembly, comprising:
   a base member including:
      a base flange having first and second opposing surfaces and first and second sides intersecting with one another; and
      a first sidewall extending from the first surface at a distance from the first and second sides; and
   a lid member, including:
      a lid flange having third and fourth opposing surfaces and third and fourth sides intersecting with one another; and
      a second sidewall extending from the third surface at a distance from the third and fourth sides, the second sidewall engageable with the first sidewall such that the first surface of the base flange and the third surface of the lid flange are in an opposing spaced-apart relationship with one another and such that the first and second sidewalls cooperate with one another to define a sample chamber,
   wherein the first sidewall includes at least one port fluidly coupled with the sample chamber.

5. The sample vessel assembly of claim 1, wherein the base flange is substantially square.

6. The sample vessel assembly of claim 5, wherein the lid flange is substantially square.

7. A sample vessel assembly, comprising:
   a base member including:
      a base flange having first and second opposing surfaces and first and second sides intersecting with one another; and
      a first sidewall extending from the first surface at a distance from the first and second sides; and
   a lid member, including:
      a lid flange having third and fourth opposing surfaces and third and fourth sides intersecting with one another; and
      a second sidewall extending from the third surface at a distance from the third and fourth sides, the second sidewall engageable with the first sidewall such that the first surface of the base flange and the third surface of the lid flange are in an opposing spaced-apart relationship with one another and such that the first and second sidewalls cooperate with one another to define a sample chamber, wherein the base flange further includes at least one opening formed therein, the at least one opening separated a first distance from the first and second sides and a second distance from the first sidewall.

8. A sample vessel assembly, comprising:
a base member including:
a base flange having first and second opposing surfaces and first and second sides intersecting with one another; and
a first sidewall extending from the first surface at a distance from the first and second sides; and
a lid member, including:
a lid flange having third and fourth opposing surfaces and third and fourth sides intersecting with one another; and
a second sidewall extending from the third surface at a distance from the third and fourth sides, the second sidewall engageable with the first sidewall such that the first surface of the base flange and the third surface of the lid flange are in an opposing spaced-apart relationship with one another and such that the first and second sidewalls cooperate with one another to define a sample chamber,
wherein the first sidewall further includes at least one port fluidly coupled with the sample chamber, and wherein at least one of the first and second sides further includes at least one notch formed therein and positioned substantially centered relative to the at least one port.

9. The sample vessel assembly of claim 8, wherein the at least one notch is at least one first notch, and wherein at least one of the third and fourth sides includes at least one second notch substantially aligned with the at least one first notch.

10. A sample vessel assembly, comprising:
at least two sample vessel assemblies attached on one another, each of the sample vessels comprising:
a base member including:
a base flange having first and second opposing surfaces and first and second sides intersecting with one another; and
a first sidewall extending from the first surface at a distance from the first and second sides; and
a lid member, including:
a lid flange having third and fourth opposing surfaces and third and fourth sides intersecting with one another; and
a second sidewall extending from the third surface at a distance from the third and fourth sides, the second sidewall engageable with the first sidewall such that the first surface of the base flange and the third surface of the lid flange are in an opposing spaced-apart relationship with one another and such that the first and second sidewalls cooperate with one another to define a sample chamber,
wherein each of the base flanges further includes at least one opening formed therein and at least one attachment protrusion extending from the second surface adjacent to the at least one opening.

11. The sample vessel assembly stack of claim 10, wherein each of the lid flanges further includes at least one opening for matingly receiving the at least one attachment protrusion of the base flange of another sample vessel assembly.

* * * * *